(12) United States Patent
Seiler et al.

(10) Patent No.: US 10,195,084 B2
(45) Date of Patent: Feb. 5, 2019

(54) CENTERING TECHNIQUE FOR A CUTTING LASER FOR REFRACTIVE OPHTHALMIC SURGERY

(71) Applicant: Novartis AG, Basel (CH)

(72) Inventors: Theo Seiler, Erlangen (DE); Christof Donitzky, Eckental (DE); Peter Riedel, Erlangen (DE); Jörg Klenke, Nürnberg (DE)

(73) Assignee: Novartis AG (CH)

( * ) Notice: Subject to any disclaimer, the term of this patent is extended or adjusted under 35 U.S.C. 154(b) by 235 days.

(21) Appl. No.: 15/173,174

(22) Filed: Jun. 3, 2016

(65) Prior Publication Data

US 2017/0100282 A1    Apr. 13, 2017

(30) Foreign Application Priority Data

Oct. 12, 2015 (DE) .................. 10 2015 013 237

(51) Int. Cl.
*A61F 9/008* (2006.01)
*A61B 3/10* (2006.01)
*A61F 9/009* (2006.01)

(52) U.S. Cl.
CPC .......... *A61F 9/0084* (2013.01); *A61B 3/102* (2013.01); *A61B 3/1005* (2013.01); *A61B 3/1015* (2013.01); *A61F 9/008* (2013.01); *A61F 9/009* (2013.01); *A61F 9/00827* (2013.01); *A61F 9/00836* (2013.01); *A61F 2009/00842* (2013.01); *A61F 2009/00851* (2013.01); *A61F 2009/00872* (2013.01)

(58) Field of Classification Search
USPC ........................................... 606/4–5
See application file for complete search history.

(56) References Cited

U.S. PATENT DOCUMENTS

| | | | |
|---|---|---|---|
| 2010/0130966 A1* | 5/2010 | Brownell | A61B 3/1005 606/4 |
| 2011/0034911 A1 | 2/2011 | Bischoff et al. | |
| 2013/0211387 A1 | 8/2013 | Riedel et al. | |

FOREIGN PATENT DOCUMENTS

| | | |
|---|---|---|
| CN | 101810528 A | 8/2010 |
| CN | 103501686 A | 1/2014 |
| WO | 2010000278 A1 | 1/2010 |
| WO | 2013004255 A1 | 1/2013 |

* cited by examiner

*Primary Examiner* — Nicole F Johnson
(74) *Attorney, Agent, or Firm* — Keiko Ichiye, Esq.

(57) ABSTRACT

According to certain embodiments, a method for laser cutting treatment of a human eye comprises: determining position information of a pupil center of the eye in relation to a point of minimal corneal thickness in an undeformed state of the eye; locating the point of minimal corneal thickness in a flattened state of the eye, in which the eye is deformed by contact with a patient adapter of a laser device; and aligning a pulse firing pattern for laser radiation pulses of the laser device, based on a position of the located point of minimal corneal thickness and the determined position information. In embodiments, the pulse firing pattern represents, for example, a lenticular or doughnut-shaped intracorneal tissue volume which is to be removed from the cornea of the eye.

18 Claims, 3 Drawing Sheets ical Background

The present disclosure relates in general to the field of machining of an eye using pulsed laser radiation, and relates in particular to a technique for aligning a pulse firing pattern relative to an eye of a patient.

Methods for laser-assisted surgery on the human eye include many different types of surgery, and have the objective of improving vision, treating eye disease, or both. Conventional known types of surgery include, for example, laser-assisted in situ keratomileusis (LASIK), corneal transplantation (keratoplasty), intracorneal lenticule extraction, implantation of intracorneal ring segments, implantation of corneal inlays, and the like, to name only a few. In certain forms of laser-assisted ophthalmic surgery, it is necessary to make one or more incisions in the eye to be treated. Such incisions may be made in human eye tissue using ultrashort pulsed laser radiation, wherein a beam focus of the laser radiation is guided in time and space according to a pulse firing pattern, so that the radiation pulses arrive at the eye at appropriate locations for achieving a desired cutting geometry in the eye which is represented by the pulse firing pattern.

For the success of a surgical procedure, it must be ensured that each incision is made at the correct location in the tissue of the eye. The pulse firing pattern should therefore be defined with reference to the position of one or more eye features, which may be located at the time of the surgical procedure by means of suitable imaging technology. Examples of eye features include a pupil center, an iris structure, the limbus, and a sclera structure (such as a blood vessel) of the eye.

Conventional cutting laser systems which are used for making an incision in a human eye are typically equipped with a patient adapter (patient interface) which is used for immobilizing the eye to be treated opposite from an opening at which the laser radiation is output from the laser radiation system. This radiation output opening may be situated, for example, on an output side of a focusing objective of the laser system. The patient adapter includes an applanation plate or some other contact element that provides a contact surface for the eye. When the eye is pressed against the contact element and the outer surface of the eye fits closely against the contact surface of the contact element, the cornea of the eye undergoes deformation. When the patient adapter has, for example, an applanation plate with a planar contact surface, the cornea is deformed in a flattened state.

BRIEF SUMMARY OF THE DISCLOSURE

An object of the present disclosure is to provide a novel technique to allow a pulse firing pattern to be aligned with respect to a predefined corneal point.

According to one aspect, a method for the laser cutting treatment of a human eye is provided, comprising:
determining position information of a reference feature of the eye in relation to a given corneal point in an undeformed state of the eye;
locating the given corneal point in a deformed state of the eye;
aligning a pulse firing pattern for laser radiation pulses of a laser device, based on a position of the located given corneal point in a coordinate system of the laser device and the determined position information.

In certain embodiments, the deformed state of the eye is a state in which the cornea of the eye is deformed by contact with a contact element of a patient adapter of the laser device. The deformed state is, for example, a flattened state of the cornea.

In certain embodiments, the given corneal point represents a site of minimal thickness of the cornea. Upon contact of the eye with a contact element of a patient adapter and the resulting flattening or other type of deformation of the cornea, the thickness profile of the cornea generally does not change, or in any event changes only negligibly. A human cornea typically has a site of minimal thickness which is situated approximately in the area of the vertex of the cornea. This site of minimal corneal thickness can be located in the undeformed state of the cornea as well as in the deformed (for example, flattened) state of the cornea, for example by means of pachymetry (thickness measurement) of the cornea.

In certain embodiments, the reference feature represents a pupil center of the eye. In a state in which the eye to be treated is coupled to a patient adapter of the laser device, imaging of the iris of the eye through the patient adapter may be difficult or even impossible. Accordingly, pupil detection, and, based thereon, a determination of the position of the pupil center, may not be possible using technical means. In contrast, as long as the eye is not yet coupled to the patient adapter, and therefore a camera (for example, a camera of an eye-tracker) is able to have an unobstructed field of view of the eye, camera-based pupil detection may be possible. Therefore, in certain embodiments, position information which represents the position of the pupil center relative to the site of minimal corneal thickness may be determined in a preoperative phase, based on measurements at a diagnostic station. In a subsequent operative phase, after the eye has been coupled to the patient adapter, the site of minimal corneal thickness may be located by means of an imaging method carried out through the patient adapter, and based on the point of minimal corneal thickness which is thus located, the position of the pupil center in the coordinate system of the laser device may be computed, using the previously determined position information. The pulse firing pattern may be subsequently aligned with reference to the position of the pupil center in the coordinate system of the laser device which is thus computed. For example, the pulse firing pattern may define coordinate information at a plurality of firing positions for each laser radiation pulse, the coordinate information relating to a certain coordinate origin. The alignment may take place, for example, by basing the coordinate information of the firing positions on the computed position of the pupil center in the coordinate system of the laser device as a new coordinate origin. In other embodiments, the reference feature represents a vertex of the eye or a specific position which can be identified with reference to the pupil center and/or the vertex, e.g. a position located midway or at another point along an imaginary line connecting the pupil center and the vertex. In certain embodiments, a user interface is provided to enable a user to select one of a plurality of different reference features (e.g. pupil center, vertex) that are available for selection by the user.

In certain embodiments, the position information represents a two-dimensional position of the reference feature in relation to the given corneal point. In other words, the position information represents the position of the reference feature in a two-dimensional plane (expressed, for example, by x and y coordinates) in relation to the given corneal point.

In certain embodiments, the pulse firing pattern represents a cutting pattern which defines a lenticular or doughnut-shaped intracorneal tissue volume. By extracting such an intracorneal tissue volume from beneath the natural outer surface of the eye, the refractive properties of the cornea may be altered, and thus, defective vision (myopia, hyperopia, for example) may be corrected. The position of the tissue volume in the eye to be extracted may be defined in relation to an axis which extends through the pupil center. For a precise correction of visual defects, the cutting pattern, which is to separate the tissue volume, to be removed, from the surrounding corneal tissue, must be made in the eye with precise alignment with the pupil center. Any misalignment with respect to the pupil center may result in further visual defects. The method described here is therefore not only, but in particular, suited for refractive laser surgical treatment methods in which a cutting pattern to be made in the eye requires a precise alignment relative to the pupil center.

In certain embodiments, the step of determining position information includes: performing imaging of the eye by means of Scheimpflug tomography or optical coherence tomography in the undeformed state of the eye, wherein first image data are generated; and evaluating the first image data in order to locate the given corneal point and the reference feature.

In certain embodiments, the step of locating the given corneal point may include: performing imaging of the eye by means of optical coherence tomography or Scheimpflug tomography in the deformed state of the eye, wherein second image data are generated; and evaluating the second image data in order to locate the given corneal point.

In certain embodiments, the step of alignment may include: determining a position of the reference feature in the coordinate system, based on the position of the located given corneal point and the determined position information; and aligning the pulse firing pattern relative to the determined position of the reference feature.

In certain embodiments, the method also includes: applying laser radiation pulses having a pulse duration in the range of picoseconds, femtoseconds, or attoseconds to the cornea of the eye according to the aligned pulse firing pattern.

According to a further aspect, an apparatus for performing eye treatments is provided, comprising: a first imaging device which is configured for generating first image data for an eye to be treated, while the eye is in an undeformed state; a second imaging device which is configured for generating second image data for the eye while the eye is in a deformed state; a laser apparatus which is configured for providing pulsed laser radiation; and a control device which is configured for determining, based on the first image data, position information of a reference feature of the eye in relation to a given corneal point, locating the given corneal point, based on the second image data, aligning a pulse firing pattern for laser radiation pulses of the laser apparatus, based on a position of the located given corneal point in a coordinate system of the laser apparatus and the determined position information, and controlling the laser apparatus for delivering laser radiation pulses according to the aligned pulse firing pattern.

In certain embodiments, the second imaging device is configured for generating the second image data while the cornea of the eye is deformed by contact with a contact element of a patient adapter which is coupled to the laser apparatus. The contact element has, for example, a planar contact surface for the eye. Alternative shapes of the contact surface are likewise conceivable, such as a concave or convex shape.

In certain embodiments, the first imaging device is configured for generating the first image data by means of Scheimpflug tomography or optical coherence tomography in the undeformed state of the eye, and the control device is configured for evaluating the first image data in order to locate the given corneal point and the reference feature.

In certain embodiments, the second imaging device is configured for generating the second image data by means of optical coherence tomography or Scheimpflug tomography in the deformed state of the eye, the control device being configured for evaluating the second image data in order to locate the given corneal point.

In certain embodiments, the control device is configured for determining a position of the reference feature in the coordinate system, based on the position of the located given corneal point and the determined position information, and aligning the pulse firing pattern relative to the determined position of the reference feature.

In certain embodiments, the laser radiation pulses provided by the laser device have a pulse duration of picoseconds, femtoseconds, or attoseconds.

BRIEF DESCRIPTION OF THE DRAWINGS

The invention is explained in greater detail below with reference to the appended drawings, which show the following.

DETAILED DESCRIPTION OF THE DRAWINGS

Figure 1:
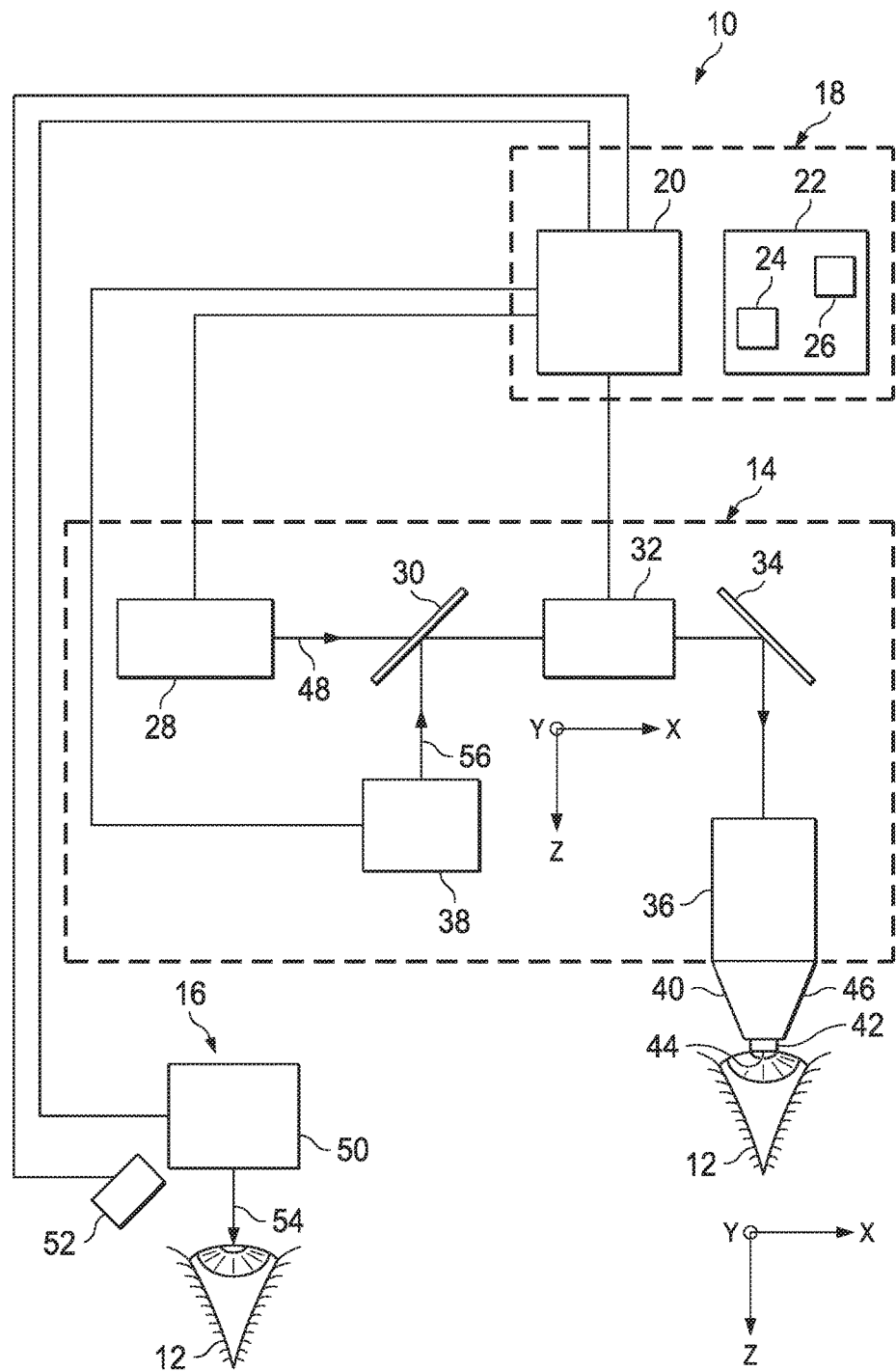
FIG. 1 schematically illustrates components of an apparatus for performing laser surgical treatments of the human eye according to one exemplary embodiment.

Reference is first made to FIG. 1. An apparatus, denoted in general by reference numeral 10, for performing laser surgical treatments of a human eye 12 by means of pulsed laser radiation is shown in FIG. 1. In certain embodiments, the apparatus 10 may align a pulse firing pattern (which represents a cutting pattern to be made in the eye 12) in relation to a pupil center of the eye 12, so that firing coordinates of the pulse firing pattern are in a defined relationship with the pupil center. In these embodiments, the pupil center is located indirectly by locating a given corneal point by evaluation of pachymetry data, and, based on the given corneal point which is located in this manner, locating the pupil center, using a preoperatively determined position relationship between the given corneal point and the pupil center. A laser device is subsequently appropriately controlled in order to direct laser radiation pulses onto a target area in the eye 12 according to the aligned pulse firing pattern.

In the exemplary embodiment shown in FIG. 1, the apparatus 10 includes a laser apparatus 14, a diagnostic imaging device 16 (first imaging device), and a computer system 18 which contains a control computer 20 and a memory 22. The memory 22 may be designed as a single memory component, or may comprise a plurality of physically separate memory components. The memory 22 stores a laser control program 24 as well as data 26 (for example, image data, measurement data, patient data, etc.).

In the example case shown, the eye 12 is a human eye. In certain embodiments, the pulsed laser radiation provided by the laser apparatus 14 is directed onto a target area situated in the cornea of the eye 12, in order to generate at that location a laser-induced optical breakdown (LIOB) and resulting photodisruption in the tissue of the target area. Corneal layers include, from the anterior to the posterior, the epithelium, Bowman's layer, the stroma, Descemet's membrane, and the endothelium. The target area may, for example, lie at least partially within the stroma.

In certain embodiments, the pulse firing pattern defines a corneal element which may be removed (extracted) in order to make a refractive correction. For example, the corneal element may represent a lenticular or doughnut-shaped tissue volume. This corneal element may be generated below the epithelium of the cornea. For example, the corneal element may be generated in the stroma of the eye 12. In other embodiments, the corneal element may be replaced, such as in the case of keratoplasty (corneal transplantation). In this case, the corneal element may be, for example, a pathological tissue volume which is replaced by a correspondingly shaped corneal element from a healthy donor cornea. In yet other embodiments, the pulse firing pattern may define one or more pockets which are provided for receiving an implant. The implant may be, for example, an intracorneal ring segment (often referred to as Intac) or a corneal inlay (Kamra implant).

The laser apparatus 14 includes a laser source 28, a beam splitter 30, a scanner 32, one or more stationary optical mirrors 34, a focusing objective 36, and a treatment pachymetry device (second imaging device) 38, which may be coupled to one another in the manner shown in FIG. 1. The laser apparatus 14 is detachably coupled to a patient adapter 40. The patient adapter 40 is used as a mechanical interface between the laser apparatus 14 and the eye 12 in order to immobilize the eye 12 relative to the laser apparatus 14. The patient adapter 40 has a contact element 42 with a contact surface 44 for the eye 12. The contact element 42 is permeable to the laser radiation of the laser apparatus 14; i.e., the laser radiation is delivered through the contact element 42 in the direction of the eye 12. The contact element 42 is mounted in the area of the narrower end of a conically expanding adapter element 46, which in the area of its wider end is coupled to the focusing objective 36 in a positionally stable but detachable manner.

The laser source 28 generates a laser beam 48 which consists of a series of ultrashort radiation pulses. Within the meaning of the present disclosure, "ultrashort pulse" means a radiation pulse having a pulse duration of less than one nanosecond, and being in the range of picoseconds, femtoseconds, or attoseconds, for example. The focal point of the laser beam 48 may generate a laser-induced optical breakdown (LIOB) in tissue of the cornea or other portions of the eye 12. The laser beam 48 may have a vacuum wavelength in the range of approximately 300 to approximately 1900 nanometers (nm), for example a wavelength in the range of 300-650 nm or in the range of 650-1050 nm or in the range of 1050-1250 nm or in the range of 1100-1900 nm. The laser beam 48 may have a comparatively small focal volume; for example, it may have a focal diameter of approximately 5 microns (μm) or less.

The beam splitter 30, the scanner 32, the optical mirror(s) 34, and the focusing objective 36 are situated in succession in the beam path of the laser beam 48. The scanner 32 allows transversal and longitudinal position displacement of the focal point of the laser beam 48 under the control of the computer system 18. In the present case, "transversal" refers to a direction that is orthogonal with respect to the direction of propagation of the laser beam 48; "longitudinal" refers to the direction of propagation of the laser beam 48. A transversal plane may be denoted as the x, y plane, while the longitudinal direction may be denoted as the z direction. In certain embodiments, the contact surface 44 of the patient adapter 40 is in an x, y plane.

The scanner 32 may transversally guide the laser beam 48 in any suitable manner. For example, the scanner 32 may include a pair of galvanometrically activated scanner mirrors which are tiltable about mutually perpendicular axes. Alternatively, the scanner 32 may include an electro-optical crystal which is able to electro-optically guide the laser beam 48. The scanner 32 may also guide the focal point of the laser beam 48 in the longitudinal direction in any suitable manner. For example, the scanner 32 may contain a longitudinally adjustable lens, a lens of variable refractive power, or a deformable mirror in order to change the z position of the beam focus. The components of the scanner 32 which are responsible for the focal adjustment do not have to be combined in a single compact unit. Instead, they may be distributed along the beam path of the laser beam 48. Thus, for example, the function of the x, y deflection of the scanner 32 may be implemented in a separate scanner module, while the function of the z focal adjustment of the scanner 32 may be structurally implemented in a beam expander, not illustrated in greater detail, which is situated in the beam path of the laser beam 48, between the laser source 28 and the mentioned x, y scanner module.

The focusing objective 36 focuses the laser beam 48 onto a point which lies on the contact surface 44 of the patient adapter 40 or beyond the contact surface 44 (within the eye 12). The focusing objective 36 is designed as an f-theta objective, for example.

The contact surface 44 of the contact element 42 is used for fitting closely against the cornea of the eye 12. In the example case shown, the contact surface is planar, so that it results in flattening of the cornea; however, in alternative designs it may have any other arbitrary shape (convex, concave, for example).

The laser apparatus 14, the computer 18, and the patient adapter 40 together may be regarded as a laser device within the meaning of the present disclosure.

The diagnostic imaging device 16 is situated, for example, at a separate diagnostic station (spatially apart from a treatment station at which the laser apparatus 14 is present), and in the example case shown includes a tomography device 50 which operates according to the optical coherence tomography (OCT) principle or Scheimpflug principle, and one or more eye-tracker cameras 52. Only one such camera 52 is shown in FIG. 1; in the following discussion, the camera 52 is always referred to only in the singular. The camera 52 delivers image data, which represent recorded images of the eye 12, to the computer system 18. The control computer 20 carries out image processing based on the delivered image data in order to recognize movements of the eye 12. The image processing includes pupil recognition, in which the pupil of the eye 12 is recognized in the recorded images and the position of the pupil center in a coordinate system of the diagnostic imaging device 16 is computed. The tomography device 50 directs a measuring light beam 54 onto the eye 12 (under control of the control computer 20 in accordance with recognized eye movements) and receives reflected light from the eye 12. The tomography device 50 delivers tomography data to the computer system 18, from which the control computer 20 is able to compute, inter alia, the corneal thickness for a plurality of corneal locations. Based on the tomography data, the control computer 20 may accordingly create a two-dimensional thickness profile of the cornea of the eye 12. Moreover, the control computer 20 is configured to identify, based on the tomography data of the tomography device 50, a pupil center of the eye 12.

The tomography by means of the tomography device 50 is performed preoperatively in a state in which the cornea of the eye 12 is undeformed, i.e., not flattened or otherwise deformed by contact with a contact element. After the preoperative tomography is performed, the patient must go from the diagnostic station to the treatment station where the laser apparatus 14 is set up. The data which are preoperatively recorded by means of the diagnostic imaging device 16 and/or the data derived therefrom by the control computer 20 are stored in the memory 22.

The treatment pachymetry device 38 is part of the laser apparatus 14, and is used for performing pachymetry of the eye 12 at the treatment station, but this time in a deformed state of the eye 12 when the eye is in contact with the contact surface 44 of the contact element 42. Similarly as for the tomography device 50, the pachymetry device 38 may operate according to the OCT principle or Scheimpflug principle. It emits a measuring light beam 56 which is coupled into the beam path of the laser beam 48 by means of the beam splitter 30. The pachymetry device 38 delivers pachymetry data to the computer system 18, where the control computer 20 computes a two-dimensional thickness profile of the cornea in the deformed state thereof based on the delivered pachymetry data. The pachymetry is performed by means of the pachymetry device 38 before the laser treatment of the eye 12 begins.

The control computer 20 controls the scanner 32 and the laser source 28 according to the control program 24. The control program 24 contains computer code which represents the pulse firing pattern, and appropriately instructs the laser apparatus 14 to suitably control the focal point of the laser beam 48 in time and space, so that a cutting pattern corresponding to the pulse firing pattern results in the cornea of the eye 12.

Figure 2A:
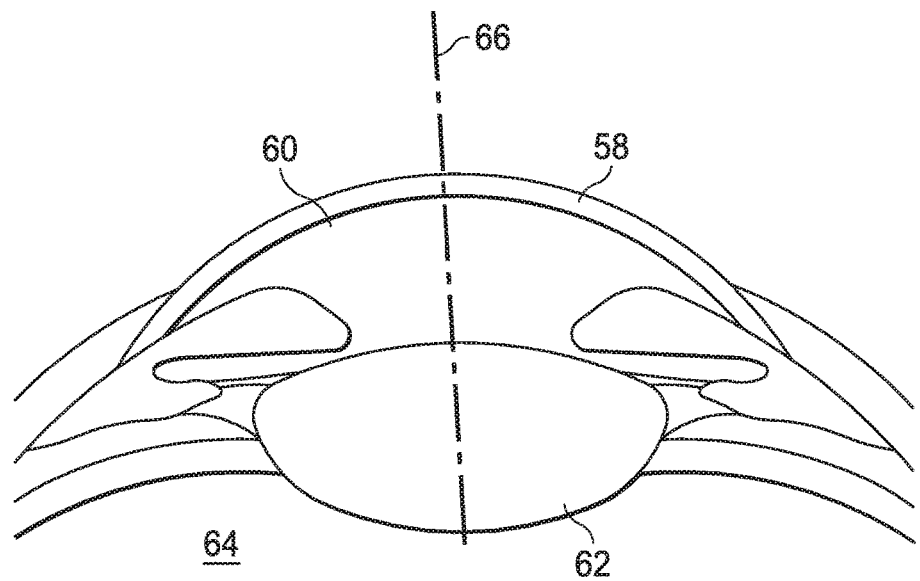
FIG. 2A shows a sectional illustration of the anterior portion of a human eye in an undeformed state.

FIG. 2A shows an example illustration of the eye 12 in an undeformed state. The eye 12 includes a cornea 58, an anterior eye chamber 60, a lens 62, and a vitreous body 64. Likewise shown is a representative axis 66 of the eye 12 which, for example, may be the visual axis which connects the foveola of the eye 12 to the pupil center.

Figure 2B:
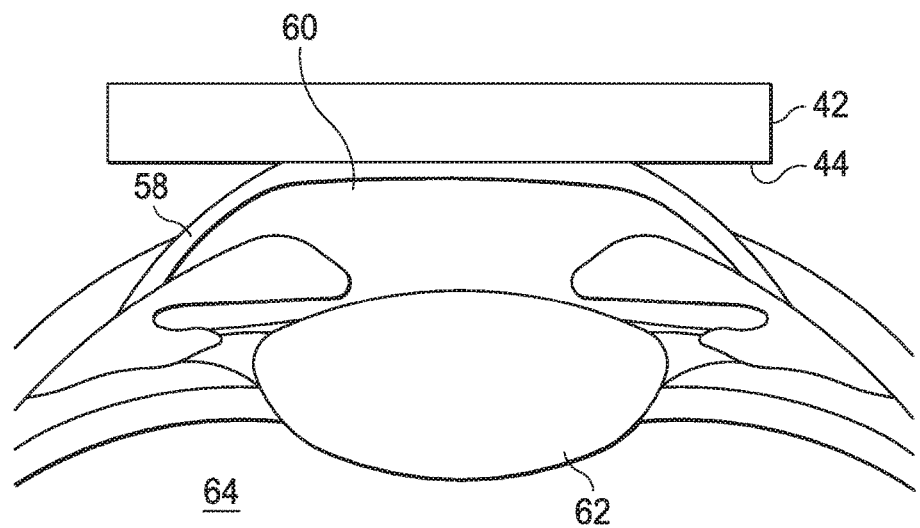
FIG. 2B shows a sectional illustration of the same anterior portion of the eye as in FIG. 2A, but in a flattened state of the cornea.

FIG. 2B shows a view by way of example of the eye 12 when it is flattened by contact with the contact surface 44 of the contact element 42.

Figure 3:
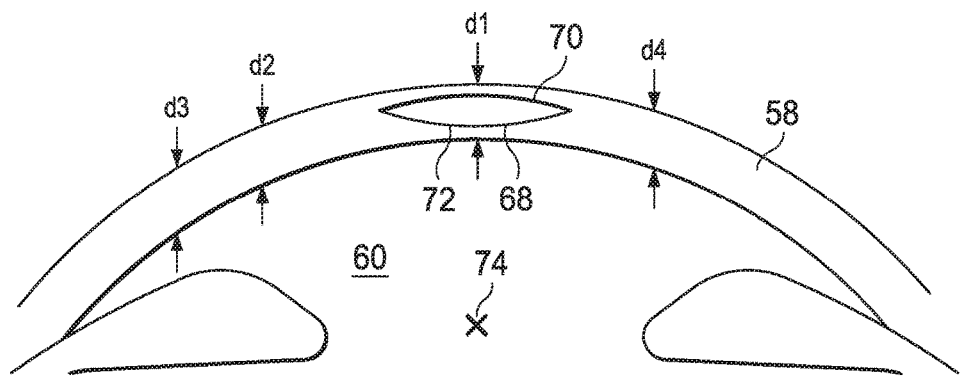
FIG. 3 shows an enlarged sectional view of an anterior portion of a human eye in order to schematically illustrate corneal thickness variations, and FIG. 4 schematically shows a position-based relationship between a site of minimal corneal thickness and a pupil center in an x, y plane.

FIG. 3 illustrates how the thickness of the cornea 58 may vary at various locations on the cornea. Typically, the corneal thickness is smaller in a central area of the cornea, and increases toward the edge areas of the cornea 58. For example, the cornea 58 has a thickness d1 in the central area, and has thicknesses d2, d3, d4 in areas farther from the center, where d1<d2, d3, d4. The fundamental increase in thickness of the cornea 58 from the center (apex) to the periphery may be overlaid by additional local thickness variations due to irregularities at the anterior surface and/or the posterior surface of the cornea 58. Notwithstanding the existence of these local fluctuations in thickness, the cornea 58 has a site of minimal corneal thickness close to the center which may be unambiguously identified. In the example case in FIG. 3, it is assumed that this site of minimal thickness is situated where the dimension d1 is depicted. Identifying the site of minimal corneal thickness is possible based, for example, on an absolute thickness value and/or on a pattern of the thickness distribution of the cornea.

Likewise shown in FIG. 3 is an example of a lenticular tissue volume 68 which is to be extracted from the cornea 58 for the purpose of eliminating defective vision of the eye. The tissue volume 68 is delimited by a curved front surface 70 and a curved rear surface 72. A planning module, which may be implemented in the control program 24 of the computer 18, plans the position, size, and shape of the tissue volume 68 according to the need for refractive correction for the patient. The planning module generates the pulse firing pattern on the basis of the planned position, size, and shape of the tissue volume 68.

For successfully improving the vision, the cutting pattern represented by the pulse firing pattern must have a precisely defined position within the cornea 58. For this purpose, the mentioned planning module plans the position of the tissue volume 68 in relation to an unambiguous reference feature of the eye 12, the reference feature being the pupil center in the example case under consideration here. The pupil center is schematically indicated by reference numeral 74 in FIG. 3 strictly for purposes of illustration.

Figure 4:
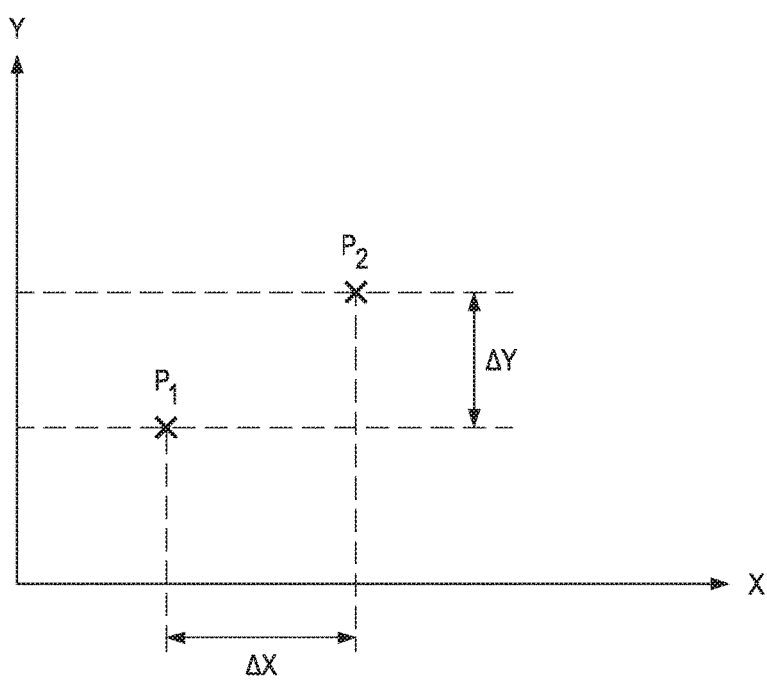

In the applanated state of the eye 12, i.e., when the eye 12 lies against the contact element 42 corresponding to the illustration in FIG. 1, detection of the pupil center 74 by technical means may be difficult or not possible at all. In contrast, the site of minimal corneal thickness (for example, the site at which the corneal thickness has the value d1 in FIG. 3) may be located in the applanated (deformed) state of the cornea 58, namely, by evaluating the pachymetry data delivered by the pachymetry device 38. In order to still be able to locate the pupil center 74 in the applanated state of the cornea 58 and align the pulse firing pattern with respect to the pupil center in the xyz coordinate system of the laser apparatus 14, the control computer 20, based on the data delivered by the diagnostic imaging device 16 (in particular the tomography data delivered by the tomography device 50), determines position information which represents a position of the pupil center relative to the site of minimal corneal thickness in a plane, which corresponds to an x, y plane of the xyz coordinate system of the laser apparatus 14. In this regard, reference is made to FIG. 4. In FIG. 4, two points $P_1$, $P_2$ are depicted in an x, y plane, and, based on an example used strictly for illustration, show the positions of the site of minimal corneal thickness ($P_1$) and the pupil center ($P_2$) in the x, y plane. Based on the tomography data of the tomography device 50, the control computer 20 determines x, y coordinates for the site of minimal corneal thickness (point $P_1$) and x, y coordinates for the pupil center (point $P_2$). Based on the x, y coordinates of the points $P_1$ and $P_2$ determined in this way, the control computer 20 determines the distance between the two points in the x direction and in the y direction (expressed by the values $\Delta x$, $\Delta y$, respectively, in FIG. 4). In the present example case, the values for Δx and Δy form the position information which is determined by the control computer 20 for the relative position of the pupil center in relation to the site of minimal corneal thickness.

After the patient has been placed below the laser apparatus 14 and his/her eye 12 has been properly coupled to the patient adapter 40, the computer 18 performs further pachymetry of the cornea 58 by means of the pachymetry device 38. The control computer 20 determines, based on the pachymetry data of the pachymetry device 38, the position of the site of minimal corneal thickness in an x, y plane of the xyz coordinate system. Using the previously determined values Δx for the x distance and Δy for the y distance, the control computer 20 then computes the position of the pupil center in the x, y plane by adding Δx and Δy, with the correct algebraic signs, to the x, y coordinates of the site of minimal corneal thickness. The control computer 20 obtains x, y coordinates for the pupil center in this way. These x, y coordinates of the pupil center are used by the control computer 20 as a reference point for aligning the pulse firing pattern. After the pulse firing pattern has been aligned (which may also be referred to as coordinate correction) and optionally as a function of further conditions, the control computer 20 directs the laser apparatus 14 to deliver radiation pulses according to the aligned pulse firing pattern.

The invention claimed is:

1. Method for laser cutting treatment of a human eye, comprising:
   determining position information of a reference feature of the eye in relation to a given corneal point representing a site of minimal thickness of the cornea in an undeformed state of the eye;
   locating the given corneal point in a deformed state of the eye in which the cornea of the eye is deformed by contact with a contact element of a patient adapter; and
   aligning a pulse firing pattern for laser radiation pulses in an x,y plane of the xyz coordinate system of a laser device, based on a position of the located given corneal point representing the site of minimal thickness in the xyz coordinate system of the laser device and the determined position information.

2. Method according to claim 1, wherein the deformed state is a flattened state of the cornea.

3. Method according to claim 1, wherein the reference feature represents a pupil center of the eye.

4. Method according to claim 1, wherein the position information represents a two-dimensional position of the reference feature in relation to the given corneal point.

5. Method according to claim 1, wherein the pulse firing pattern represents a cutting pattern which defines a lenticular or doughnut-shaped intracorneal tissue volume.

6. Method according to claim 1, wherein the determination of position information includes:
   performing imaging of the eye by means of Scheimpflug tomography or optical coherence tomography in the undeformed state of the eye, whereby first image data are generated; and
   evaluating the first image data in order to locate the given corneal point and the reference feature.

7. Method according to claim 1, wherein locating the given corneal point includes:
   performing imaging of the eye by means of optical coherence tomography or Scheimpflug tomography in the deformed state of the eye, whereby second image data are generated; and
   evaluating the second image data in order to locate the given corneal point.

8. Method according to claim 1, wherein the alignment includes:
   determining a position of the reference feature in the coordinate system, based on the position of the located given corneal point and the determined position information; and
   aligning the pulse firing pattern relative to the determined position of the reference feature.

9. Method according to claim 1, further comprising:
   applying laser radiation pulses having a pulse duration in the range of picoseconds, femtoseconds, or attoseconds to the cornea of the eye according to the aligned pulse firing pattern.

10. Apparatus for performing eye treatments, comprising:
    a first imaging device configured to generate first image data for an eye to be treated, while the eye is in an undeformed state;
    a second imaging device configured to generate second image data for the eye while the eye is in a deformed state, a contact element adapted to place the cornea of the eye in the deformed state by contact;
    a laser apparatus configured to provide pulsed laser radiation; and
    a control device configured to:
       determine based on the first image data, position information of a reference feature of the eye in relation to a given corneal point representing a site of minimal thickness of the cornea;
       locate the given corneal point, based on the second image data;
       align a pulse firing pattern for laser radiation pulses in an x,y plane of the xyz coordinate system of the laser apparatus, based on a position of the located given corneal point representing a site of minimal thickness in the xyz coordinate system of the laser apparatus and the determined position information; and
       control the laser apparatus for delivering laser radiation pulses according to the aligned pulse firing pattern.

11. Apparatus according to claim 10, wherein the contact element has a planar contact surface for the eye.

12. Apparatus according to claim 10, wherein the reference feature represents a pupil center of the eye.

13. Apparatus according to claim 10, wherein the position information represents a two-dimensional position of the reference feature in relation to the given corneal point.

14. Apparatus according to claim 10, wherein the pulse firing pattern represents a cutting pattern which defines a lenticular or doughnut-shaped intracorneal tissue volume.

15. Apparatus according to claim 10, wherein:
    the first imaging device is configured to generate the first image data by Scheimpflug tomography or optical coherence tomography in the undeformed state of the eye; and
    the control device is configured to evaluate the first image data in order to locate the given corneal point and the reference feature.

16. Apparatus according to claim 10, wherein:
    the second imaging device is configured to generate the second image data by optical coherence tomography or Scheimpflug tomography in the deformed state of the eye; and
    the control device is configured to evaluate the second image data in order to locate the given corneal point.

17. Apparatus according to claim 10, wherein the control device configured to:

determine a position of the reference feature in the coordinate system, based on the position of the located given corneal point and the determined position information; and align the pulse firing pattern relative to the determined position of the reference feature.

18. Apparatus according to claim 10, wherein the laser radiation pulses provided by the laser apparatus have a pulse duration in the range of picoseconds, femtoseconds, or attoseconds.

* * * * *